United States Patent
Nikula et al.

(10) Patent No.: US 12,369,827 B2
(45) Date of Patent: Jul. 29, 2025

(54) BIO-SIGNAL SKIN CONTACT SENSOR APPARATUS AND METHOD OF MAKING SKIN CONTACT

(71) Applicant: Bittium Biosignals Oy, Kuopio (FI)

(72) Inventors: Arto Nikula, Oulu (FI); Juha Myllykangas, Kuopio (FI)

(73) Assignee: Bittium Biosignals Oy, Kuopio (FI)

( * ) Notice: Subject to any disclaimer, the term of this patent is extended or adjusted under 35 U.S.C. 154(b) by 371 days.

(21) Appl. No.: 18/120,764

(22) Filed: Mar. 13, 2023

(65) Prior Publication Data

US 2024/0306970 A1    Sep. 19, 2024

(51) Int. Cl.
*A61B 5/25* (2021.01)

(52) U.S. Cl.
CPC ............ *A61B 5/25* (2021.01); *A61B 2562/16* (2013.01)

(58) Field of Classification Search
CPC ................................. A61B 5/25; A61B 5/6833
See application file for complete search history.

(56) References Cited

U.S. PATENT DOCUMENTS 3,713,435 A * 1/1973 Szpur .................. A61B 5/25
                                                      600/397
5,489,215 A * 2/1996 Wright .................. A61B 5/25
                                                      439/86
2023/0355153 A1* 11/2023 Nikula .................. A61B 5/256

\* cited by examiner

*Primary Examiner* — William J Levicky
(74) *Attorney, Agent, or Firm* — Nixon & Vanderhye PC

(57) ABSTRACT

A bio-signal skin contact apparatus comprises a first layer, a second layer with adhesive for a skin contact, and a middle layer that is elastic and located between and in contact with the first layer and the second layer. Each of one or more hole structures comprise a first hole through the first layer, a second hole through the second layer and a third hole through the middle layer. The first, second and third holes of a single hole structure of the at least one hole structure are overlapping. A connector structure is partly within the hole, the connector structure comprising an extension, which extends above the level of the first layer, and a cavity for a sensor within the connector structure. The extension performs a bayonet connection with a counter-connector. The connector structure comprises an aperture through the extension in a level of the middle layer. A compartment is filled with flowable material within the hole structure, the flowable material being in contact with and covered by the first layer. The flowable material flows through the aperture into the cavity for the flowable material to become in contact with both skin and the sensor in response to tightening action of the bayonet connection that causes compression to the bio-signal skin contact apparatus at the connector structure and deformation of the compartment based on elasticity of the middle layer for causing pressure to the flowable material.

9 Claims, 2 Drawing Sheets

BIO-SIGNAL SKIN CONTACT SENSOR APPARATUS AND METHOD OF MAKING SKIN CONTACT

FIELD

The invention relates to a bio-signal skin contact sensor apparatus and a method of making a skin contact.

BACKGROUND

When a bio-signal sensor is attached in contact with skin its ability to sense the bio-signal depends on the interface between the sensor and the skin. The interface may vary as a function of time, and that is particularly true when the person who or the mammal in general which carries the sensor makes moves or is constantly moving.

As an example, electrically conductive electrodes of EKG (ElectroCardioGram) and EEG (ElectroEncephaloGram) measurement devices are typically covered by electrically conductive gel to improve electric contact between the electrodes and the skin. The gel may be separately attached to the electrodes or to the locations of electrodes on the skin. Alternatively, the gel may be on each of the electrodes under a removable film that is removed before attachment. The removable film is only loosely attached with the electrode element because it must be easily detachable, and that is why the protection the removable film brings to the gel is only limited. When the electrodes are attached to the skin, the gel layer as a whole is exposed to air, dust, microbes and other air-born contaminants. The gel layer may also accidentally touch some undesired surface before the attachment to a predetermined location on the skin. If the electrode slips on the skin before a proper attachment, the gel transferred to the skin prevents the adhesive to fix the electrode to the skin. Hence, an improvement would be welcome.

BRIEF DESCRIPTION

The present invention seeks to provide an improvement in the measurements.

The invention is defined by the independent claims. Embodiments are defined in the dependent claims.

If one or more of the embodiments is considered not to fall under the scope of the independent claims, such an embodiment is or such embodiments are still useful for understanding features of the invention.

LIST OF DRAWINGS

Example embodiments of the present invention are described below, by way of example only, with reference to the accompanying drawings, in which FIG. 1 illustrates an example of a bio-signal skin contact apparatus;

DESCRIPTION OF EMBODIMENTS

The following embodiments are only examples. Although the specification may refer to "an" embodiment in several locations, this does not necessarily mean that each such reference is to the same embodiment(s), or that the feature only applies to a single embodiment.

Single features of different embodiments may also be combined to provide other embodiments. Furthermore, words "comprising" and "including" should be understood as not limiting the described embodiments to consist of only those features that have been mentioned and such embodiments may also contain features/structures that have not been specifically mentioned. All combinations of the embodiments are considered possible if their combination does not lead to structural or logical contradiction.

It is to be understood that at least some of the figures and descriptions are simplifications to certain extent and illustrate mainly elements that are relevant for understanding what is claimed, while eliminating, for purposes of clarity, other elements that may be included in what is claimed. However, because such elements are well known in the art, and/or because they do not facilitate a better understanding of the claimed features, a description of such elements is not provided herein.

Figure 1:
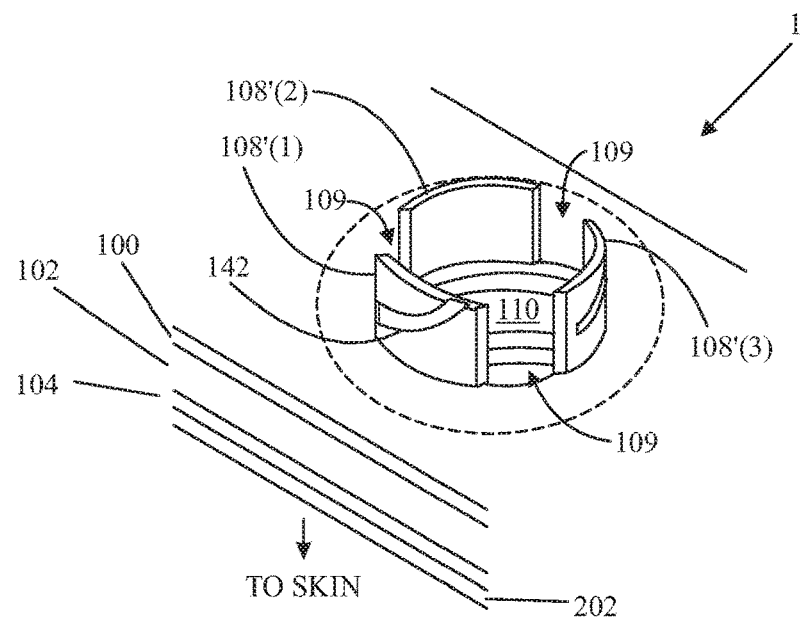
Figure 2:
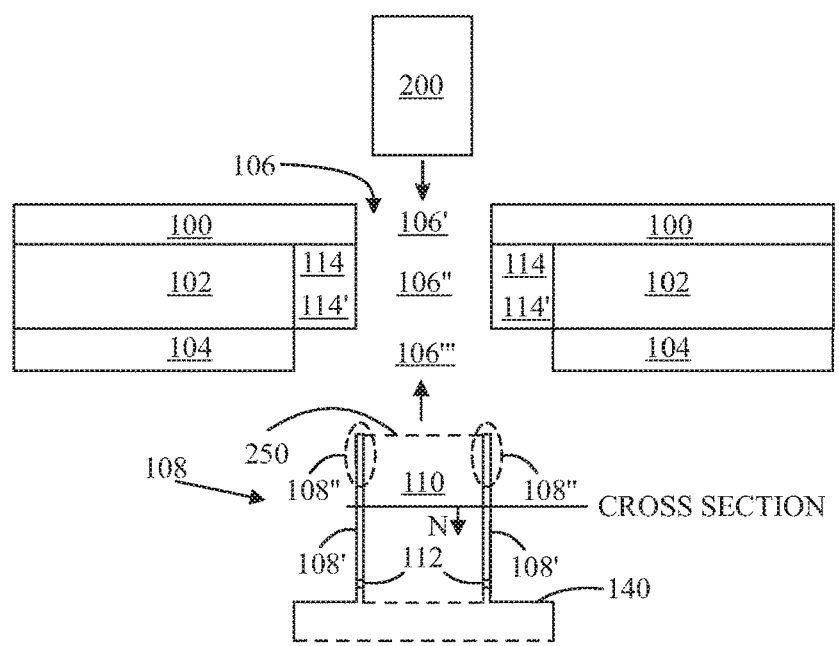
FIG. 2 illustrates an example of the bio-signal skin contact apparatus with the parts separated from each other.
Figure 3:
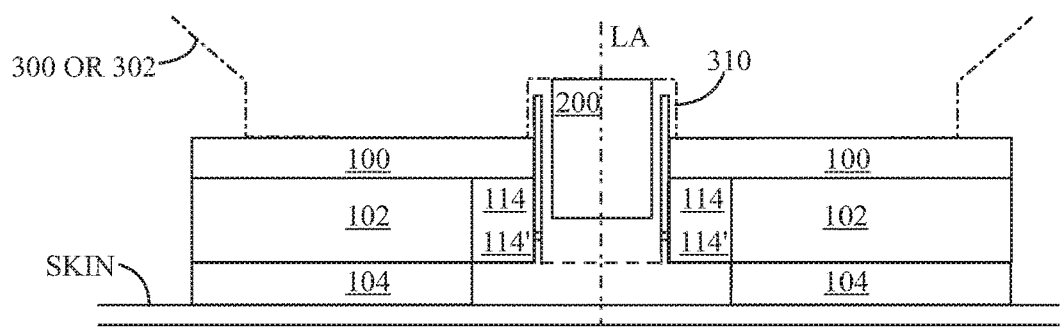
FIG. 3 illustrates an example of the bio-signal skin contact apparatus with parts put together.

FIGS. 1 to 3 illustrate a bio-signal skin contact apparatus 10 that may comprise a layered film that is attached to the skin of a patient. The bio-signal skin contact apparatus 10 may be a patch electrode structure or a patch sensor structure. The bio-signal skin contact apparatus 10 may be attached to the skin using adhesive that may be on a surface of the bio-signal skin contact apparatus 10. The bio-signal skin contact apparatus 10 comprises a first layer 100, a second layer 104 with adhesive for a skin contact, and a middle layer 102 that is elastic and compressible. The first layer 100 may be flexible. That the middle layer 102 is compressible means that its volume becomes smaller under pressure, and such a change in volume without breakage is enabled by elasticity of the middle layer 102. The middle layer 102 is located between and in contact with the first layer 100 and the second layer 104. The adhesive on a surface of the second layer 104 may be covered with a protective film such as back liner 202, which may be removed before the bio-signal skin contact apparatus 10 is attached to the skin.

Alternatively, the adhesive may be separately spread on a surface of the bio-signal skin contact apparatus 10 or on the skin for the attachment. In this kind of example, the second layer 104 does not necessarily have adhesive but instead, as explained, it is applied separately when the attachment to the skin is performed. Also in this example, the protective film such as the back liner 202 may be omitted although it may also be utilized.

The bio-signal skin contact apparatus 10 also comprises at least one hole structure 106. Each of the hole structures 106 comprise a first hole 106' through the first layer 100, a second hole 106" through the second layer 104 and a third hole 106''' through the middle layer 102. The first, second and third holes 106', 106", 106''' of a single hole structure 106 of the at least one hole structure 106 are configured to be at least partially overlapping in a ready-made bio-signal skin contact apparatus 10.

The bio-signal skin contact apparatus 10 additionally comprises a connector structure 108 partly within the hole 106. The connector structure 108 comprises cavity wall structure 108'. The cavity wall structure 108 comprises an extension 108", which is configured to extend above the level of the first layer 100.

The connector structure 108 comprises also a cavity 110 within the cavity wall structure 108. The cavity wall structure 108 may be a continuous wall. Then a cross section of the cavity wall structure 108 closes an area within the wall structure, a normal N of the area of the cross section being parallel to a longitudinal axis LA of the cavity 110. Alternatively, the cavity wall structure 108 may be partially continuous round the longitudinal axis LA of the cavity 110, which is illustrated in FIG. 1. That means, the cavity wall structure 108 has two or more separate sub-wall structures 108'(1), 108'(2), 108'(3), which are separated by a gap 109 although each of them is integrated with a floor-structure 140 common to all the sub-wall structures 108'(1), 108'(2), 108'(3) at one end of the sub-wall structures 108'(1), 108'(2), 108'(3).

The cavity 110 is for a sensor 200 that is configured to locate within or be inserted into the connector structure 108. The wall structure 108' is configured to perform a bayonet connection with a counter-connector 310. The bayonet connection is enabled with a helical groove 142 on the wall structure 108'. The groove 142 may be on an outer side or an inner side of the wall structure 108'. The helix of the groove 142 leads toward the second layer 104 and skin in response to tightening the connection with the counter-connector 310 which has an extension structure such as a pin fitted to enter and travel within the helical groove 142. Tightening the connection moves the sensor 200 toward the second layer 104 and the skin. The groove 142 may have a quick locking mechanism at the end of the groove 142. A person skilled in the art is familiar with the bayonet connection based on a helical groove, locking mechanism and its counterpart, per se. The connector structure 108 additionally comprises at least one aperture 112 through the wall structure 108' in a level of the middle layer 102.

Moreover, the bio-signal skin contact apparatus 10 comprises at least one compartment 114 that is filled with flowable material 114'. Medium of the flowable material 114' may be liquid, gel or higher viscosity material similar to wax or resin that can keep its shape in NTP (Normal Temperature and Pressure). The at least one compartment 114 is within the hole structure 106, and the flowable material 114' is in contact with and covered by the first layer 100. In an embodiment, the flowable material 114' may reside also in a wider volume than the at least one compartment 114.

The flowable material 114' is configured to flow through the at least one aperture 112 into the cavity 110 for the flowable material 114' to become in contact with both the skin and the sensor 200 in response to a connection and locking action of the bayonet connection. The connection with a movement of the counterpart toward the second layer 104 while the counterpart rotates with the pin in the helical groove 142 causes compression to the bio-signal skin contact apparatus 10 at the connector structure 108 and deformation of the compartment 114 based on elasticity of the middle layer 102. The compression makes the size of the compartment 114 smaller and that causes pressure to the flowable material 114'.

In an embodiment, the flowable material 114' has at least one of the following: thermal conductivity, electrical conductivity, antisepticity, microbial effect, at least one reagent for sweat and local anesthetic effect.

In an embodiment, the sensor 200 may be configured to sense temperature which in the prior art has challenges. The flowable material 114' may improve contact and thermal conductivity between the sensor 200 and the skin when the flowable material 114' is between and in contact with both the sensor 200 and the skin.

In an embodiment, the sensor 200 may be configured to measure electrical conductivity of the skin. The flowable material 114' may improve contact and electrical conductivity between the sensor 200 and the skin when the flowable material 114' is between and in contact with both the sensor 200 and the skin.

Microbes may cause variation in connection with the sensor 200 and the skin. The variation may become the larger the longer the connection between the sensor 200 and the skin. Alternatively or additionally, the sensor 200 may be such that it penetrates through the skin which may increase a risk of infection. An infection or a mere microbe growth may deteriorate accuracy of a measurement of the sensor 200, and an uncontrolled increase of microbes may also be a health issue. In an embodiment, a well-controlled or predetermined amount of antiseptic flowable material 114' may be automatically dosed between the sensor 200 and the skin in conjunction with the application of the skin contact apparatus 10 to the skin. Antiseptic flowable material includes one or more antimicrobial substances that limit possibilities of infection, sepsis, and/or decaying of the skin and/or other organs by the microbes. Still, the antiseptic flowing material does not damage skin. The antiseptic flowable material may be considered to have a disinfecting effect.

In an embodiment, the flowable material 114' may cause a microbial effect on skin. In an embodiment, the flowable material 114' may increase growth of one or more microbes. In an embodiment, the flowable material 114' may increase growth of one or more microbes over other microbes. In that manner, the flowable material 114' may favor desired or predetermined microbes over other microbes. In an embodiment, the sensor 200 may, in turn, be configured to detect the microbes that have increased and/or that have been favored. In an embodiment, the sensor 200 may be configured to output a signal that carries information on a number or amount of the microbes that have increased and/or that have been favored as a function of time. Alternatively or additionally, the sensor 200 may be configured to output a signal that carries information on a number or amount of the microbes that have decreased and/or that have been disfavored as a function of time.

In an embodiment, the flowable material 114' may include at least one reagent for sweat. The sensor 200, in turn, may be configured to detect one or more products of reaction between sweat and the at least one reagent. In that way, the bio-signal gives information on sweat and biological processes of the body.

In an embodiment the flowable material 114' may include local anesthetic for an anesthetic effect. For example, if the sensor 200, which may include a needle or the like, penetrates the skin, it may cause pain that the anesthetic may relieve.

The sensor 200 may include one or more sensor units for measuring one or more of thermal conductivity, electrical conductivity, antisepticity, microbial effect, and sweat based on reaction with the one or more reagent. The thermal and electrical conductivity measurements may be performed using semiconductor sensor. Detection of microbes and/or products based on a reaction between the at least one reagent and sweat may be performed using an optical sensor. The optical detection may be based on spectrum, for example. The optical detection may be based on fluorescence and/or Raman radiation, for example. The sensor 200 may have on optical radiation source for the measurements. A person skilled in the art is familiar with various types of bio-signal sensors, per se.

In an embodiment, the bio-signal skin contact apparatus 10 may comprise a back liner 202 attached to the second layer 104. The back liner 202 may be detachable for enabling attachment of the skin contact apparatus 10 to the skin. The back liner 202 may be polymer film, for example.

Figure 4:
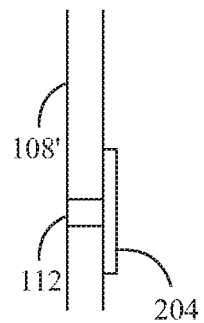
FIG. 4 illustrates an example of the wall structure with an aperture and a seal.

In an embodiment an example of which is illustrated in FIG. 4, the at least one aperture 112 may comprise a seal 204 that is configured to break and/or detach under pressure caused by the bayonet connection for enabling the flowable material 114 to flow to the cavity 110 and into connection to the skin and the sensor 200. In FIG. 4, the seal 204 is drawn in a surface of the wall structure 108'. However, the seal 204 may also reside at the aperture 112 within the wall structure 108'. The seal 204 may comprise a polymer film that may be thin. The pressure range at which the seal 204 breaks may be determined based on a thickness of the seal and/or material of the seal 204. In a similar manner, a pressure range at which the seal 204 detaches from the wall 108' may be determined based on adhesive and curing of adhesive. A person skilled in the art is familiar with breakage of a seal and adhesive strength, per se.

In an embodiment, a thickness of the middle layer 102 is in a range 0.5 mm to 2 mm.

In an embodiment, the middle layer 102 comprises elastic foam.

In an embodiment an example of which is illustrated in FIG. 3, the bio-signal skin contact apparatus 100 may connect with a bio-signal measurement apparatus 300 directly or indirectly through the bayonet connection. The direct connection may connect the bio-signal skin contact apparatus 100 and the bio-signal measurement apparatus 300 directly together. The connection means both physical and electric connection such that the electric connection enables electric data transfer from the sensor 200 to the bio-signal measurement apparatus 300. In the indirect connection, the bio-signal skin contact apparatus 100 may be connected with an adapter 302 that is further connectable with the bio-signal measurement apparatus 300. The bio-signal measurement apparatus 300 and/or the adapter 302 have a counter-connector for the bayonet connection mechanism of the bio-signal skin contact apparatus 10.

In an embodiment, the wall structure 108' is covered with a sealing film 250. The sealing film 250 covers the wall structure 108' fully such that air cannot be in contact with the flowable material 114' even if the at least one aperture 112 has no seal 204. Namely, if the at least one aperture 112 is small enough to with respect to viscosity of the flowable material 114', the flowable material 114' does not leak out from the compartment 114 without proper pressure. The sealing film 250 and the back liner 202 protect the flowable material 114' from gas exchange, dust and microbes before application of the skin contact apparatus 10 to the skin.

Together the bio-signal skin contact apparatus 10 with the sensor 200 and the bio-signal measurement apparatus form a bio-signal measurement system.

The bio-signal measurement apparatus 300 may comprise one or more processors, one or more memories including computer program code. The one or more memories and the computer program code are configured to, with the one or more processors, cause bio-signal measurement apparatus 300 to perform data processing to the bio-signal measured by the sensor 200 associated with the bio-signal skin contact apparatus 10.

The term "computer" includes a computational device that performs logical and arithmetic operations. For example, a "computer" may comprise an electronic computational device, such as an integrated circuit, a microprocessor, a mobile computing device, a laptop computer, a tablet computer, a personal computer, or a mainframe computer. A "computer" may comprise a central processing unit, an ALU (arithmetic logic unit), a memory unit, and a control unit that controls actions of other components of the computer so that steps of a computer program are executed in a desired sequence. A "computer" may also include at least one peripheral unit that may include an auxiliary memory (such as a disk drive or flash memory), and/or may include data processing circuitry.

A user interface means an input/output device and/or unit. Non-limiting examples of a user interface include a touch screen, other electronic display screen, keyboard, mouse, microphone, handheld electronic game controller, digital stylus, display screen, speaker, and/or projector for projecting a visual display.

Figure 5:
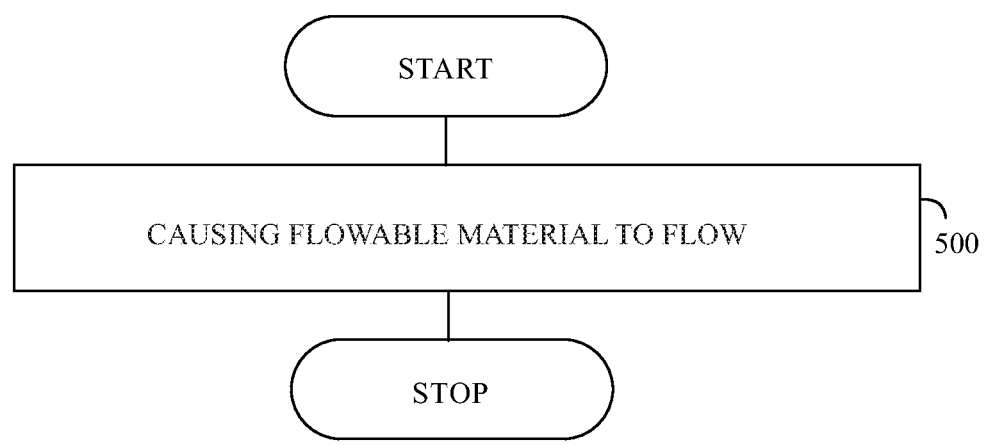
FIG. 5 illustrates of an example of a flow chart of a measuring method.

FIG. 5 is a flow chart of the measurement method. In step 500, the flowable material 114' is caused to flow through the at least one aperture 112 into the cavity 110 for the flowable material 114' to become in contact with both skin and the sensor 200 in response to a tightening action of the bayonet connection that causes compression to the bio-signal skin contact apparatus 10 at the connector structure 108 and deformation of the compartment 114 based on elasticity of the middle layer 102 for causing pressure to the flowable material.

It will be obvious to a person skilled in the art that, as technology advances, the inventive concept can be implemented in various ways. The invention and its embodiments are not limited to the example embodiments described above but may vary within the scope of the claims.

What is claimed is:

1. A bio-signal skin contact apparatus, wherein the bio-signal skin contact apparatus comprises
    a first layer, a second layer with adhesive for a skin contact, and a middle layer that is elastic and located between and in contact with the first layer and the second layer;
    at least one hole structure, each of the hole structures comprising a first hole through the first layer, a second hole through the second layer and a third hole through the middle layer, the first, second and third holes of a single hole structure of the at least one hole structure being overlapping;
    a connector structure partly within the hole, the connector structure comprising an extension, which is configured to extend above the level of the first layer, and a cavity for a sensor within the connector structure, the extension being configured to perform a bayonet connection with a counter-connector, the connector structure comprising at least one aperture through the extension in a level of the middle layer;
    a compartment filled with flowable material within the hole structure, the flowable material being in contact with and covered by the first layer; and
    the flowable material is configured to flow through the at least one aperture into the cavity for the flowable material to become in contact with both skin and the sensor in response to tightening action of the bayonet connection that is configured to cause compression to the bio-signal skin contact apparatus at the connector structure and deformation of the compartment based on elasticity of the middle layer for causing pressure to the flowable material.

2. The apparatus of claim 1, wherein the flowable material has at least one of the following: thermal conductivity, electrical conductivity, antisepticity, local anesthetic effect, at least one reagent for sweat.

3. The apparatus of claim 1, wherein the bio-signal skin contact apparatus comprises a back liner attached to the second layer, the back liner being detachable for enabling attachment of the skin contact apparatus to the skin.

4. The apparatus of claim 1, wherein the at least one aperture comprises a seal that is configured to break and/or detach under pressure caused by the bayonet connection for enabling the flowable material to flow to the cavity and into connection to the skin and the sensor.

5. The apparatus of claim 1, wherein a thickness of the middle layer is in a range 0.5 mm to 2 mm.

6. The apparatus of claim 1, wherein in that the middle layer comprises elastic foam.

7. The apparatus of claim 1, wherein the bio-signal skin contact apparatus is configured to connect with a bio-signal measurement apparatus directly or indirectly through the bayonet connection, the direct connection connecting the bio-signal skin contact apparatus and the bio-signal measurement apparatus directly together, and the indirect connection connecting the bio-signal skin contact apparatus with an adapter that is connectable with the bio-signal measurement apparatus.

8. A bio-signal measurement system, wherein the bio-signal measurement system comprises a bio-signal skin contact apparatus that comprises
- a first layer, a second layer with adhesive for a skin contact, and a middle layer that is elastic and located between and in contact with the first layer and the second layer,
- at least one hole structure, each of the hole structures comprising a first hole through the first layer, a second hole through the second layer and a third hole through the middle layer, the first, second and third holes of a single hole structure of the at least one hole structure being overlapping,
- a connector structure partly within the hole, the connector structure comprising an extension, which is configured to extend above the level of the first layer, and a cavity for a sensor within the connector structure, the extension being configured to perform a bayonet connection with a counter-connector, the connector structure comprising at least one aperture through the extension in a level of the middle layer,
- flowable material within the hole structure in contact with and covered by the first layer, and
- the flowable material is configured to flow through the at least one aperture into the cavity for the flowable material to become in contact with both skin and the sensor in response to a locking action of the bayonet connection that is configured to cause the bio-signal skin contact apparatus to compress at the connector structure based on elasticity of the middle layer for causing pressure to the flowable material; and
- a bio-signal measurement apparatus and the bio-signal skin contact apparatus are configured to connect directly or indirectly with each other through the bayonet connection.

9. A method of measuring a bio-signal, wherein a bio-signal skin contact apparatus comprises
- a first layer, a second layer with adhesive for a skin contact, and a middle layer that is elastic and located between and in contact with the first layer and the second layer;
- at least one hole structure, each of the hole structures comprising a first hole through the first layer, a second hole through the second layer and a third hole through the middle layer, the first, second and third holes of a single hole structure of the at least one hole structure being overlapping;
- a connector structure partly within the hole, the connector structure comprising an extension, which is configured to extend above the level of the first layer, and a cavity for a sensor within the connector structure, the extension being configured to perform a bayonet connection with a counter-connector, the connector structure comprising at least one aperture through the extension in a level of the middle layer;
- a compartment filled with flowable material within the hole structure, the flowable material being in contact with and covered by the first layer; the method comprising
- causing the flowable material to flow through the at least one aperture into the cavity for the flowable material to become in contact with both skin and the sensor in response to a tightening action of the bayonet connection that causes compression to the bio-signal skin contact apparatus at the connector structure and deformation of the compartment based on elasticity of the middle layer for causing pressure to the flowable material.

* * * * *